Figure 1:
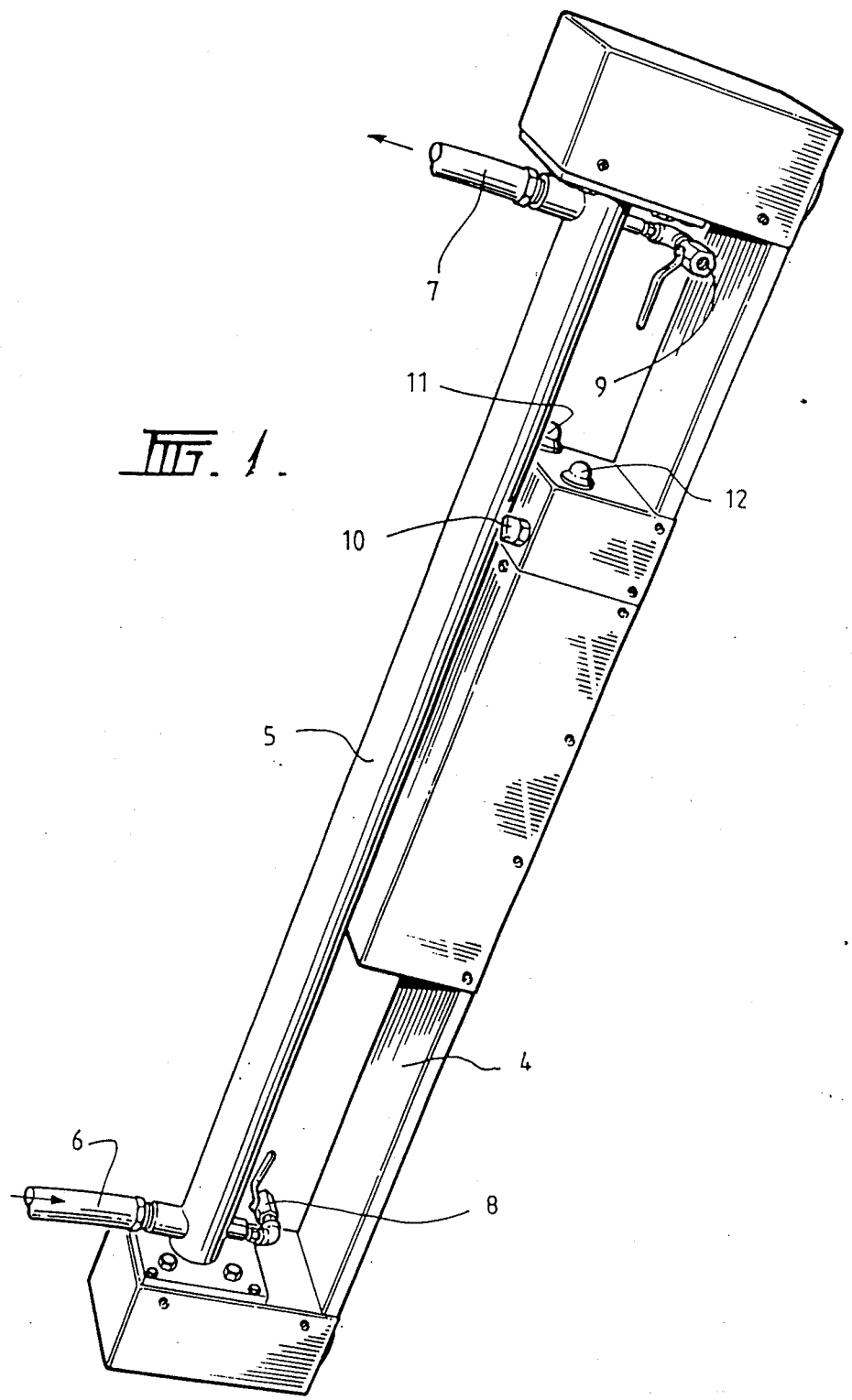

United States Patent [19]

Wilson

[11] Patent Number: 4,963,750
[45] Date of Patent: Oct. 16, 1990

[54] FLUID MEDIA STERILIZATION APPARATUS

[76] Inventor: Robert L. Wilson, 122 Fulton Road, Blackburn South, Victoria, 3130, Australia

[21] Appl. No.: 265,804

[22] PCT Filed: Dec. 9, 1987

[86] PCT No.: PCT/AU87/00417
§ 371 Date: Aug. 8, 1988
§ 102(e) Date: Aug. 8, 1988

[87] PCT Pub. No.: WO88/04281
PCT Pub. Date: Jun. 16, 1988

[30] Foreign Application Priority Data
Dec. 9, 1986 [AU] Australia .............. PH09393

[51] Int. Cl.$^5$ .......................................... G01N 21/05
[52] U.S. Cl. .................................... 250/436; 250/435; 250/438
[58] Field of Search ............. 250/435, 436, 438; 422/24

[56] References Cited

U.S. PATENT DOCUMENTS

| | | | |
|---|---|---|---|
| 3,634,025 | 1/1975 | Landry | 250/436 |
| 3,894,236 | 7/1975 | Hazelrigg | 250/435 |
| 4,101,777 | 7/1978 | Reid | 250/436 |

Primary Examiner—Bruce C. Anderson
Attorney, Agent, or Firm—Richard Bushnell

[57] ABSTRACT

A unit for the sterilization of fluid media, for example contaminated water, the unit including a source of germicidal radiation disposed substantially centrally within a tubular structure or housing, there being provided between said source of germicidal radiation and the innermost surface of said tubular structure an annular passage constituting a flow path for the fluid media. The unit is capable of providing a lethal or "killing" dosage of germicidal radiation, in excess of 99.99% "kill", even for very large flow rates of fluid media through the unit.

8 Claims, 2 Drawing Sheets

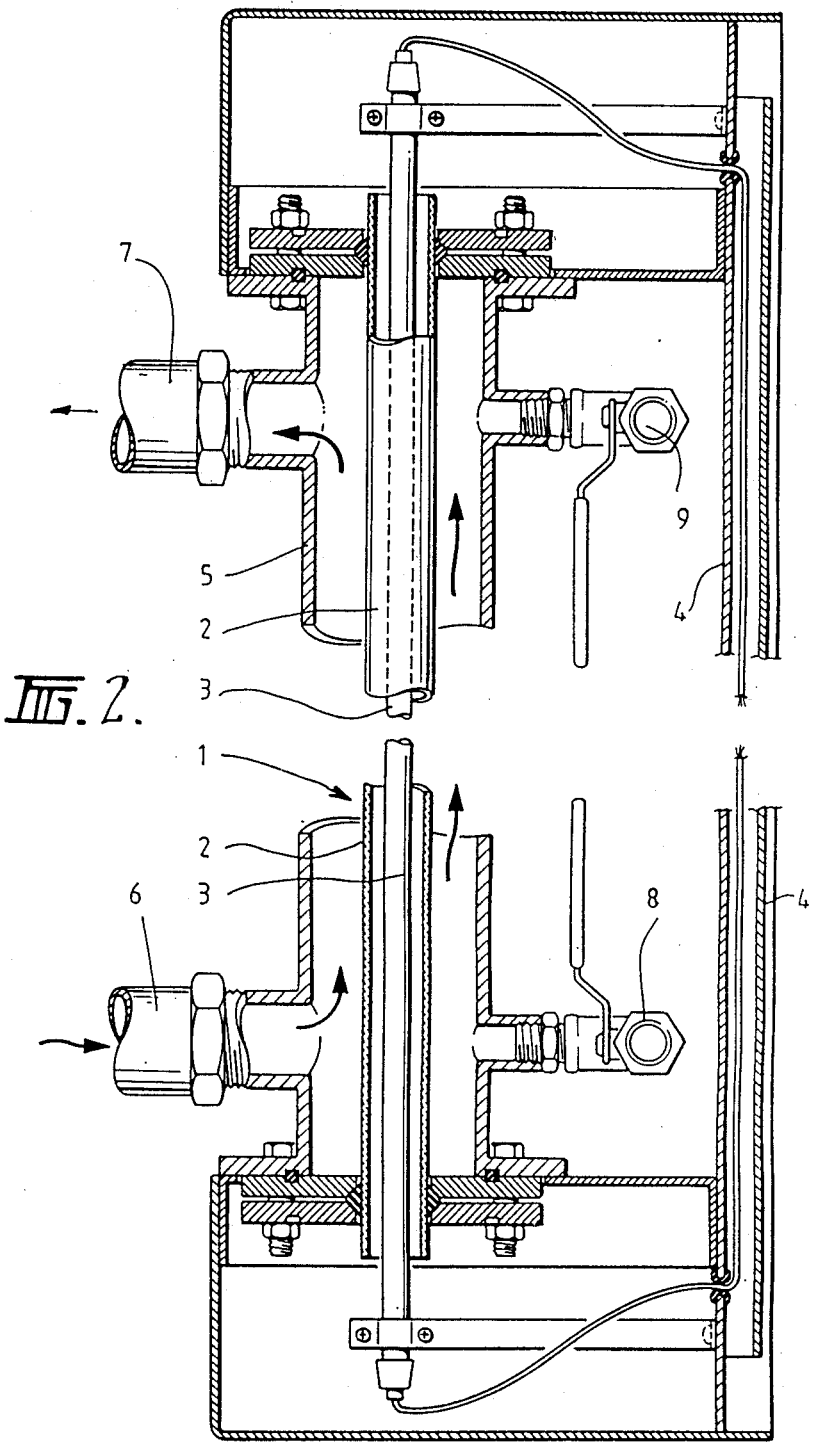

FLUID MEDIA STERILIZATION APPARATUS

The present invention relates, in general, to improvements in a process and apparatus for the sterilization of fluid media and relates more particularly, but not exclusively, to an improved process and to an improved form of apparatus or unit for the sterilization of water. The invention also relates to an improved form of what might be termed an irradiation tube for use in such sterilization processes and apparatus or units.

Throughout the ensuing description, for ease of explanation referance will be made to an especially preferred embodiment of the present invention, involving a process and apparatus for use in the sterilization of water. It should be realized, however, that the process and apparatus in accordance with the present invention will be equally suited for the sterilization of other fluid media and is not intended to be restricted solely to the preferred embodiment described.

Nowadays the need for water sterilization is regarded as being critical, for a variety of reasons. This is especially the case in less developed areas and/or areas not blessed with adequate water storage facilities. At the present time there is a considerable need for the provision of sterilizing equipment or apparatus which will be capable of handling large volumes of fluid media. Such a need has arisen, in some areas or instances, by reason of the demands for more efficient and higher productivity of the greater populations evident these days, and the increased usage of water by such larger populations. In yet other instances sterilization is made essential by virtue of the adverse effects of our modern society on ecological conditions in general.

The prior art processes, apparatus and units employed for such purposes have been found to be somewhat inappropriate, especially where an economical treatment of substantially large volumes of fluid is required, since the resorting to or reliance upon large flow media pipes has been found, in accordance with the prior art, to reduce the effective rate of efficiency of "kill" of fungi, bacteria, viruses and/or other pollutants in the fluid under consideration.

The most commonly employed method of sterilizing such fluid media, in particular water, involves exposure of that medium to what is termed a lethal dose of radiation, more especially ultra-violet radiation, of a so-called germicidal wavelength. Apparatus employed for such purposes served to expose a flow of fluid medium to radiation from a suitable source, for example an ultra-violet lamp or lamps, or a source of ultra-violet radiation of any known type. In this regard it should be realized that, in accordance with accepted and well-established standards set down by the relevant authorities, an acceptable "kill" rate for bacteria is of the order of 99.99%. A "kill" rate below that figure is not satisfactory.

The prior art or known apparatus generally involved a source of radiation (lamp or the like) disposed within a hollow tubular element and around which a fluid medium to be sterilized was adapted to be passed or flowed. Experimentation has revealed that the material actually employed for making such a hollow tubular element can have a marked effect on the efficiency of irradiation, in terms of percentage "kill" of bacteria, fungi, etc. present in the fluid medium. Tubular elements constructed from fused silica or quartz have been found to exhibit good transmissibility to ultra-violet radiation, but such fused silica or quartz elements have been found to be subject to fouling, involving the building up or accumulation of a film on such tubular elements, thereby resulting in a loss of transmissibility therethrough of the radiation employed for purposes of sterilization. Of course the greater the degree of fouling of such fused silica or quartz tubular elements, then the lesser is the transmissibility of such fouled tubes to ultra-violet radiation and, accordingly, the efficiency of operation in terms of percentage "kill" of bacteria, fungi, viruses etc. is reduced. In a practical sense it then became necessary to regularly arrange for cleaning of such fouled apparatus, thereby resulting in interruption of the procedure of sterilization.

One form of prior art ultra-violet sterilization apparatus or unit employed relied upon the use of one or more tubes or tubular elements of a material, sold under the registered trade mark "TEFLON", which is known technically as FEP (fluorinated ethylene propylene). Such material, hereinafter referred to simply as "TEFLON", has the characteristics of being transparent to germicidal rays (for example ultra-violet radiation of the requisite wavelength) and has non-stock properties such that, to all intents and purposes, effectively no film builds up on such a tube during use, thereby minimizing fouling with its inherent problems of reduced transmissibility, etc. With such an arrangement, with a source of ultra-violet radiation located within such a tube and fluid flowing therearound, it has been found that tubes of TEFLON of at least 0.02 inches thickness will allow for the passage or transmission of 81% of incident ultra-violet radiation. However, as the thickness of such tubing is increased then the degree of transmissibility of radiation to the fluid has been found to drop off somewhat alarmingly.

In a more practical sense, however, tubes of a thickness of the order of 0.02 inches also have been found to be physically incapable of withstanding the external water pressure in any apparatus which would be responsible for even a reasonable, let alone a large, volume flow treatment rate. In order to allow such tubes to be physically capable of withstanding external water pressure without unwanted collapse, it would be necessary to increase the thickness thereof, but such increase in thickness would then result in an unacceptable decrease in ultra-violet radiation transmissibility. With such arrangements, therefore, it has been found that while an acceptable degree of transmissibility of radiation can be achieved—provided of course that the tubular element was not too thick—problems were encountered in terms of constructing elements capable of withstanding external water pressure and thereby avoiding unwanted collapse. In a practical sense the thickness required for a tube of this type to be capable of withstanding the pressures associated with even a reasonable, let alone a large, volume flow of fluid media for treatment was found to give rise to a tube or tubular element which exhibited a totally inappropriate or inadequate level or degree of transmissibility for ultra-violet radiation.

In yet an alternative embodiment in accordance with the prior art a sterilization unit is employed involving a chamber having one or more such TEFLON tubes, with the medium to be irradiated being adapted to actually flow through such tubes. Arranged around such a tube or tubes are appropriate ultra-violet radiation sources. Again in a practical sense, however, such an arrangement has been found to be not particularly efficient in terms of its suffering from an unacceptable loss of incident radiation, or in other words radiation emanating from the relevant source and not incident on the TEFLON tube and hence not effective in sterilization.

It is therefore a primary object of the present invention to develop a form of sterilizing unit for fluid media which would be capable of handling large volumes of fluid media over an extended period of time to meet the demands set upon it. The invention also seeks to provide an improved form of tubular element for use in such a sterilizer unit. The present more correctly a combination of materials, which would allow for transmission of ultra-violet radiation over an extended period of time without being subjected to any photochemical change causing deterioration thereof or thereto. The invention also seeks to provide an apparatus for treating fluid media, such as water, by irradiation in a continuous operation of a flow of material through a tubular element composed of material having chemical inertness, non-stick properties and being not prone to deterioration over extended periods of operation. Finally the invention seeks to provide a sterilizing unit for sterilizing fluid media which will run efficiently over an extended period of time by in effect eliminating the need for frequent cleaning of operating parts of that unit.

The present invention seeks to overcome the problems and disadvantages associated with the prior art by providing an arrangement including a substantially centrally-arranged tubular element, preferably constructed of fused silica or quartz, having a source of ultra-violet radiation located therewithin and having water or other medium to be treated flowing therearound. In accordance with the present invention the tubular element has what is in effect a thin sheet of fluorinated ethylene propylene or TEFLON, or the equivalent material, attached thereto in any known manner.

In accordance with one aspect of the present invention, therefore, there is provided an irradiation unit for the sterilization of fluid media, said unit including: an irradiation tube constructed of a material transparent to germicidal radiation and having coated externally thereon or attached thereto a sleeve or layer of a material which is substantially transparent to germicidal ultra-violet radiation but to which impurities contained in said fluid media do not stick, said tube having a source of germicidal ultra-violet radiation disposed internally and substantially centrally thereof; and a housing of a complementary shape to said tube and disposed substantially coaxially therewith, said housing being of a larger dimension than said tube, the arrangement being such that an annular space is provided between said tube and said housing, said annular space providing a flow path for said fluid media said annular space being in the range of from 15 to 25 mm width.

In accordance with a further aspect of the present invention there is provided a sterilizer unit for fluid media, said unit including: respective inlet and outlet means for fluid media to be sterilized; at least one irradiation unit connected to and extending between said inlet and outlet means, said at least one irradiation unit including an irradiation tube constructed of a material transparent to germicidal radiation and having coated externally thereon or attached thereto a sleeve or layer of a material which is substantially transparent to germicidal ultra-violet radiation but to which impurities contained in said fluid media do not stick, said tube having a source of germicidal ultra-violet radiation disposed internally and substantially centrally thereof; and a housing of a complementary shape to said tube and disposed substantially coaxially therewith, said housing being of a larger dimension than said tube, the arrangement being such that an annular space is provided between said tube and said housing, said annular space providing a flow path for said fluid media said annular space being in the range of from 15 to 25 mm in width.

In accordance with the invention there is also provided a process for the sterilization of fluid media, using an irradiation unit and sterilizer unit as set down in the preceding paragraphs.

In order that the invention may be more clearly understood and put into practical effect there shall now be described in detail a preferred embodiment of an irradiation unit in accordance with the present invention, designed for use in a fluid medium sterilization unit. The ensuing description is given by way of non-limitative example only, and is with reference to the accompanying drawings, wherein:

FIG. 1 is a perspective view of a sterilizer unit in accordance with the present invention; and FIG. 2 is a sectional view of the unit of FIG. 1.

In accordance with the known or prior art techniques, it has been effectively universally considered that, in order to achieve a satisfactory "kill" rate of bacteria in a situation calling for an enlarged flow rate of fluid media to be sterilized, it was merely necessary to direct more "killing" or ultra-violet radiation into the actual treatment area itself. Indeed, previously employed techniques generally, if not exclusively, dictated that as desired flow rate increased, then more sources of ultra-violet radiation should be brought into play or operation. In the result, it has been the accepted practice to have from 8 to as many as 200 individual ultra-violet lamps in a sterilization unit in order to allow the unit to cope with high rates of flow of fluid medium therethrough. This practice of course has meant that known units have been extremely large and bulky, not to mention excessively expensive. The present applicant has also found, through experimentation, that problems will be experienced with such prior art units in guaranteeing that the fluid flowing through the unit is receiving a uniform, and more important a "killing", dose of ultra-violet radiation. Experimentation has shown, for example, that in a multi-tubular element unit in accordance with the known art ultra-violet radiation emanating from one lamp or source may be almost completely attenuated as it passes through and impinges on a neighbouring lamp or source. The prior art units could therefore be seen to be generally wasteful of incident ultra-violet radiation or energy, and also extremely questionable in terms of ensuring an acceptable "kill" of bacteria in the fluid being treated.

Micro-organisms of the type requiring "killing" have been found to differ significantly in their susceptibility to ultra-violet radiation, with the more resistant types perhaps requiring up to six times the dosage of more susceptible species in order to achieve an acceptable "kill". The actual dosage achieved with an ultra-violet purification chamber is subject to such factors or parameters as the nature of the hydrodynamic flow within the chamber and the variable intensity of radiation achieved at different distances from a source or lamp.

The arrangement as illustrated includes a single tubular element in accordance with the present invention, generally designated as 1, of fused silica or quartz, with a film of TEFLON 2 coated on or affixed thereto in any suitable manner. The element is so constructed as to be capable of having disposed substantially centrally thereof a source of ultra-violet radiation 3. The overall arrangement may be located in any suitable manner on a mounting frame 4. The tubular element 1 and associated film 2 will be disposed within a tubing housing 5, preferably constructed from highly polished stainless steel The stainless steel construction will guarantee an almost indefinite life for the sterilization unit. The unit in accordance with the invention is so constructed as to allow the source 3 and tubular element 1 to be easily removed when service is required, as for example when replacement is called for by reason of failure of the radiation source.

The housing 5 includes inlet and outlet means 6 and 7 respectively, preferably having some form of control valving associated thereto. In practice the inlet 6 will be connected, in any known manner, to a source of contaminated fluid, for example water to be sterilized, while the outlet 7 will be connected, again in any known manner, to a repository or reservoir for treated fluid (fluid ready for use). Preferably the housing 5 will also be provided with a drain or sample valve means 8, at or in the vicinity of the inlet 6, and an air bleed or sample valve means 9 located at or in the vicinity of the outlet 7, whereby to allow for testing of fluid with the tubular element at those locations. In the especially preferred embodiment illustrated the sterilization unit will be provided with appropriate electric circuitry and equipment to allow for operation, including an on/off switch 10, a lamp 11 or other visual and/or audio-visual means for purposes of indicating that the unit is operating (power is on) and more preferably a lamp or the like signal means 12 (either visual and/or audio) for purposes of indicating power failure or failure of the radiation source.

A tubular element in accordance with the present invention, therefore, for location within the housing 5, consists primarily of fused silica or quartz of a standard thickness. Such fused silica or quartz exhibits an eminently acceptable rate of transmission to ultra-violet radiation incident thereon from a source located therewithin. In order to effectively prevent the onset of fouling of any such quartz tubular element, in accordance with the present invention a sheath or sleeve of a suitable thickness, for example significantly less than 0.02 inches, of a suitable material, for example TEFLON, is affixed in any known manner thereto. In one embodiment a thickness 0.003 inches of such TEFLON material will be shrunk onto, sprayed onto or baked onto the quartz tubular element using known techniques. The composite tubular element thus provided has been found to exhibit approximately 87% transmission rate for ultra-violet radiation incident thereon. In an especially preferred embodiment a thickness of 0.002 inches of TEFLON or the like material may be shrunk onto, sprayed onto and/or baked onto a quartz tubular element. Such a configuration has been found to exhibit significantly greater than the aforementioned 87% transmission for ultra-violet radiation incident thereon. Such an arrangement will also be effectively proof against fouling and its inherent side-effects, and also has sufficient physical strength to withstand the effects of water pressure, etc. from fluid medium flowing therearound.

With the present applicant's arrangement the housing 5 and associated tubular element 1 preferably will be so constructed as to provide a so-called "film thickness" of the order of from 15 to 25 mm (0.59 to 0.98 inches). In other words, the annular space existing between the outer periphery or surface of the tubular element 1 and the inner surface of the housing 5 is of that order, that space in fact providing a channel for flow of media to be sterilized. In an especially preferred embodiment the film thickness will be of the order of 17 mm (0.67 inches). Experimentation has revealed that, with a film thickness of less than 15 mm (0.59 inches), the "kill" rate will be good, but the flow rate achievable will not be acceptable. On the other hand the reverse will be the case for a film thickness greater than 25 mm (0.98 inches), with such giving a good theoretical flow rate but an unacceptable "kill" rate.

Again in accordance with the present invention it has been found, experimentally, that the internal diameter of the tubular element has been found to have a pronounced effect on the efficiency of the overall sterilization unit. Indeed, for a unit, involving one such tubular element, having a source of ultra-violet radiation located therewithin, with fluid to be sterilized being adapted to flow around the tubular element in any known manner, it has been found experimentally that a tubular element having an internal diameter of from 55 to 65 mm (approximately 2.2 to 2.6 inches) is perhaps best suited for achieving an acceptable "kill" rate. Tubular elements of a larger size have been found to exhibit a substantially reduced "kill" rate for any acceptable fluid flow.

In accordance with the present invention a tubular element 1 of the aforementioned type, or alternatively a plurality or bank of any suitable number of such tubular elements 1, may be employed in an overall sterilization unit. The arrangement is such that the fluid medium to be treated is allowed to flow around such tubular element or elements 1, disposed within separate housings 5, and to be irradiated by ultra-violet radiation emanating from a source located within the or each tubular element 1. Such an arrangement has been found to allow for satisfactory irradiation or sterilization of large volumes of fluid medium, when compared with the prior art arrangements, and has also been found not to be susceptible to problems such as fouling, inefficient radiation, etc., being problems all evident in the prior art arrangements.

The arrangement in accordance with the present invention has been found, in practice, to be able to easily achieve the required "kill" rate of 99.98%, even for very high flow rates of fluid medium. This result has been achieved in an extremely cost-effective manner, without having to rely on a particularly large and bulky piece of equipment or apparatus—as was necessary with the prior art—and without having to expend wasteful amounts of energy in the generation of exorbitant amounts of ultra-violet radiation.

Finally, it is to be understood that the preceding description refers merely to a preferred embodiment of the invention, and that variations and modifications will be possible thereto without departing from the spirit and scope of the invention, the ambit of which is to be determined from the following claims.

I claim:

1. An irradiation unit for the sterilization of fluid media, said unit including: an irradiation tube constructed of a material transparent to germicidal radiation and having coated externally thereon or attached thereto a sleeve or layer of a material which is substantially transparent to germicidal ultra-violet radiation but to which impurities contained in said fluid media do not stick, said tube having a source of germicidal ultra-violet radiation disposed internally and substantially centrally thereof; and a housing of a complementary shape to said tube and disposed substantially coaxially therewith, said housing being of a larger dimension than said tube, the arrangement being such that an annular space is provided between said tube and said housing, said annular space providing a flow path for said fluid media, said annular space being in the range of from 15 to 25 mm in width.

2. The irradiation unit as claimed in claim 1, wherein said sleeve or layer is of fluorinated ethylene propylene and said tube is of fused silica or quartz.

3. The unit as claimed in claim 1, wherein said annular space is about 17 mm in width.

4. The unit as claimed in claim 1, wherein said irradiation tube has an internal diameter in the range of from 55 to 65 mm.

5. A sterilizer unit for fluid media, said unit including: respective inlet and outlet means for fluid media to be sterilized; and at least one irradiation unit connected to and extending between said inlet and outlet means, said at least one irradiation unit including an irradiation tube constructed of a material transparent to germicidal radiation and having coated externally thereon or attached thereto a sleeve or layer of a material which is substantially transparent to germicidal ultra-violet radiation but to which impurities contained in said fluid media do not stick, said tube having a source of germicidal ultra-violet radiation disposed internally and substantially centrally thereof; and a housing of a complementary shape to said tube and disposed substantially coaxially therewith, said housing being such that an annular space is provided between said tube and said housing, said annular space providing a flow path for said fluid media, said annular space being in the range of from b 15 to 25 mm in width.

6. The unit as claimed in claim 5, wherein said sleeve or layer is of fluorinated ethylene propylene and said tube is of fused silica or quartz.

7. The unit as claimed in claim 5, wherein said annular space is about 17 mm in width.

8. The unit as claimed in claim 6, wherein said irradiation tube has an internal diameter in the range of from 55 to 65 mm.

* * * * *

UNITED STATES PATENT AND TRADEMARK OFFICE
CERTIFICATE OF CORRECTION

PATENT NO. : 4,963,750
DATED : October 16, 1990
INVENTOR(S) : Robert L. Wilson It is certified that error appears in the above-identified patent and that said Letters Patent is hereby corrected as shown below:

Column 1, Line 13 " referance " it should be -- reference --

Column 3, Line 11 "The present more correctly a combination " it should be -- The present invention also seeks to find a material, or perhaps more correctly a combination --

Column 3, Line 25 " cf" it should be --of--

Column 3, Line 54 " 25 mm width " it should be -- 25 mm in width --

Column 4, Line 54 " cf " it should be -- of --

Column 6, Line 47 " 99,98% " it should be -- 99.99% --

Coulmn 8, Line 13 " from b 15 " it should be --from 15 --

Signed and Sealed this

First Day of September, 1992

*Attest:*

DOUGLAS B. COMER

*Attesting Officer*   *Acting Commissioner of Patents and Trademarks*